(12) United States Patent  
Biedermann et al.

(10) Patent No.: US 9,277,938 B2  
(45) Date of Patent: Mar. 8, 2016

(54) POLYAXIAL BONE ANCHORING SYSTEM

(75) Inventors: Lutz Biedermann, VS-Villingen (DE); Martin Meer, Vöhringen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 317 days.

(21) Appl. No.: 13/586,691

(22) Filed: Aug. 15, 2012

(65) Prior Publication Data

US 2013/0096621 A1   Apr. 18, 2013

Related U.S. Application Data

(60) Provisional application No. 61/525,097, filed on Aug. 18, 2011.

(30) Foreign Application Priority Data

Aug. 18, 2011   (EP) ...................................... 11178037

(51) Int. Cl.
*A61B 17/04* (2006.01)
*A61B 17/70* (2006.01)
*A61B 17/86* (2006.01)

(52) U.S. Cl.
CPC ............. *A61B 17/70* (2013.01); *A61B 17/7037* (2013.01); *A61B 17/8605* (2013.01)

(58) Field of Classification Search
CPC ......................... A61B 17/7037; A61B 17/8605
USPC .......................................... 606/303, 305–308
See application file for complete search history.

(56) References Cited

U.S. PATENT DOCUMENTS

| 6,736,820 B2 | 5/2004 | Biedermann et al. |
| 7,476,239 B2 | 1/2009 | Jackson |

(Continued)

FOREIGN PATENT DOCUMENTS

| CN | 101652106 A | 2/2010 |
| CN | 101754725 A | 6/2010 |

(Continued)

OTHER PUBLICATIONS

Extended European Search Report for European Application No. 11178037.5, extended European Search Report dated Dec. 8, 2011 and mailed Dec. 19, 2011 (7 pgs.).

*Primary Examiner* — Ellen C Hammond
*Assistant Examiner* — Stuart S Bray
(74) *Attorney, Agent, or Firm* — Lewis Roca Rothgerber Christie LLP

(57) ABSTRACT

A polyaxial bone anchoring system includes a receiving part having an accommodation space, a first anchoring element having a first head, a sleeve-like insert piece configured to be arranged around a portion of the first head and to be arranged in the accommodation space, a second anchoring element having a second head, and a pressure member configured to exert pressure onto the first head or the second head, wherein when one of the first anchoring element or the second anchoring element is connected to the receiving part, the connected anchoring element is pivotable relative to the receiving part and can be locked at an angle relative to the receiving part by exerting pressure with the pressure member onto the respective head of the connected anchoring element, and wherein the first bone anchoring element and the second bone anchoring element are configured to be interchangeably connectable to the receiving part.

27 Claims, 12 Drawing Sheets

(56) References Cited

U.S. PATENT DOCUMENTS

| | | |
|---|---|---|
| 7,776,067 B2 | 8/2010 | Jackson |
| 7,967,850 B2 * | 6/2011 | Jackson ......................... 606/301 |
| 8,961,568 B2 | 2/2015 | McKinley |
| 2004/0097933 A1 * | 5/2004 | Lourdel et al. .................. 606/61 |
| 2005/0049588 A1 | 3/2005 | Jackson |
| 2005/0203516 A1 | 9/2005 | Biedermann et al. |
| 2005/0216003 A1 | 9/2005 | Biedermann et al. |
| 2006/0173456 A1 | 8/2006 | Hawkes et al. |
| 2006/0271047 A1 | 11/2006 | Jackson |
| 2007/0118123 A1 | 5/2007 | Strausbaugh et al. |
| 2007/0123862 A1 | 5/2007 | Warnick |
| 2007/0293862 A1 | 12/2007 | Jackson |
| 2008/0004625 A1 * | 1/2008 | Runco et al. .................... 606/73 |
| 2008/0009862 A1 * | 1/2008 | Hoffman ......................... 606/61 |
| 2008/0015579 A1 | 1/2008 | Whipple |
| 2008/0154315 A1 | 6/2008 | Jackson |
| 2008/0177260 A1 | 7/2008 | McKinley et al. |
| 2008/0234761 A1 | 9/2008 | Jackson |
| 2008/0269809 A1 * | 10/2008 | Garamszegi .................. 606/305 |
| 2009/0062866 A1 * | 3/2009 | Jackson ......................... 606/301 |
| 2009/0093844 A1 | 4/2009 | Jackson |
| 2009/0240290 A1 | 9/2009 | Choi |
| 2009/0299414 A1 * | 12/2009 | Jackson ......................... 606/301 |
| 2010/0030280 A1 | 2/2010 | Jackson |
| 2010/0114180 A1 * | 5/2010 | Rock et al. .................... 606/308 |
| 2010/0191293 A1 | 7/2010 | Jackson |
| 2010/0211114 A1 | 8/2010 | Jackson |
| 2010/0298891 A1 | 11/2010 | Jackson |
| 2012/0035663 A1 * | 2/2012 | Jackson ......................... 606/266 |
| 2012/0123486 A1 | 5/2012 | Werner et al. |
| 2012/0136395 A1 | 5/2012 | Biedermann et al. |
| 2012/0179212 A1 | 7/2012 | Jackson et al. |
| 2013/0096620 A1 * | 4/2013 | Biedermann et al. ......... 606/279 |
| 2013/0138162 A1 * | 5/2013 | Kang et al. .................... 606/308 |
| 2013/0211465 A1 * | 8/2013 | Savage .......................... 606/308 |
| 2013/0274817 A9 * | 10/2013 | Jackson ......................... 606/309 |
| 2013/0296951 A1 * | 11/2013 | Jackson et al. ................ 606/308 |
| 2013/0325075 A1 * | 12/2013 | Jackson ......................... 606/308 |
| 2014/0058458 A1 * | 2/2014 | Barrus et al. .................. 606/308 |
| 2014/0128927 A1 | 5/2014 | Jackson |

FOREIGN PATENT DOCUMENTS

| | | |
|---|---|---|
| JP | 2006-504505 A | 2/2006 |
| JP | 2010-520024 A | 6/2010 |
| WO | WO 2004/041100 A1 | 5/2004 |
| WO | WO 2008/112114 A1 | 9/2008 |
| WO | WO 2008/124772 A1 | 10/2008 |
| WO | WO 2008/153723 A1 | 12/2008 |
| WO | WO 2009/015100 A2 | 1/2009 |

* cited by examiner

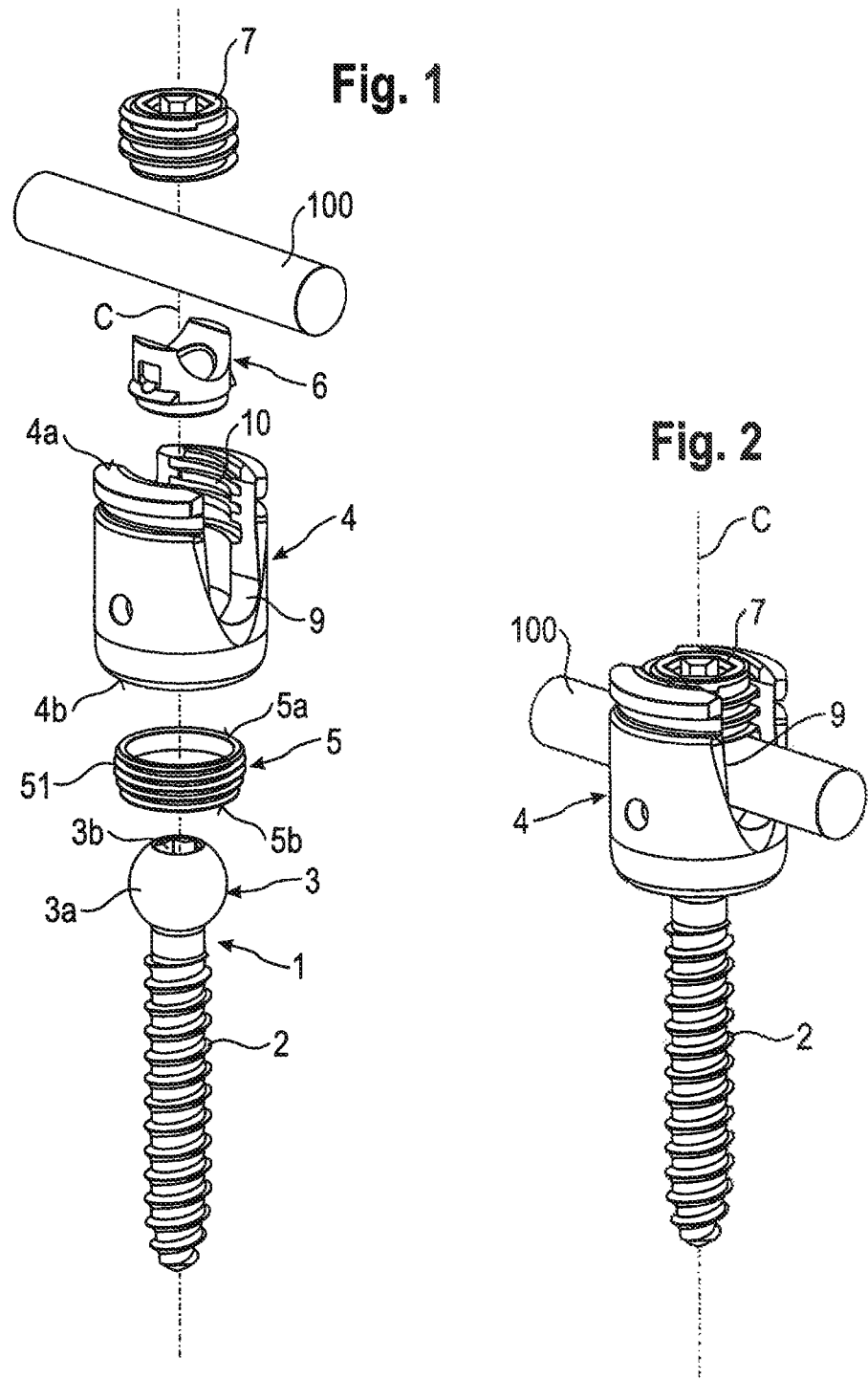

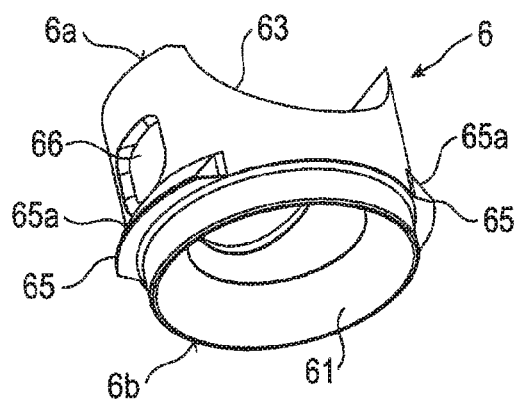
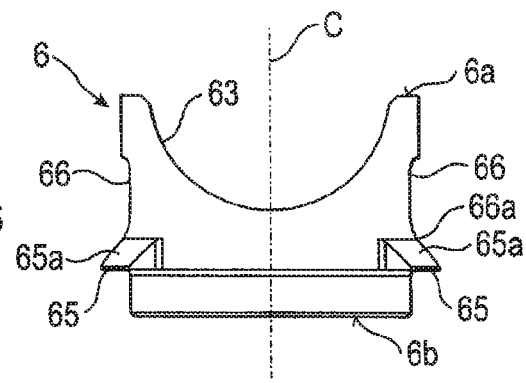
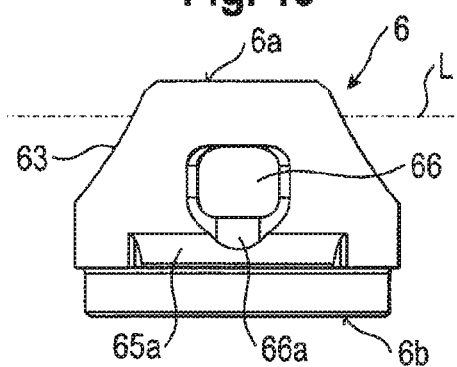
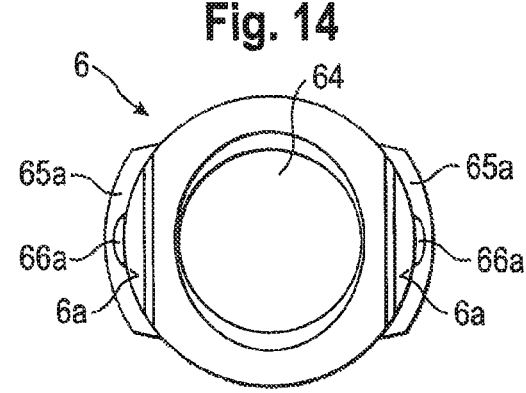
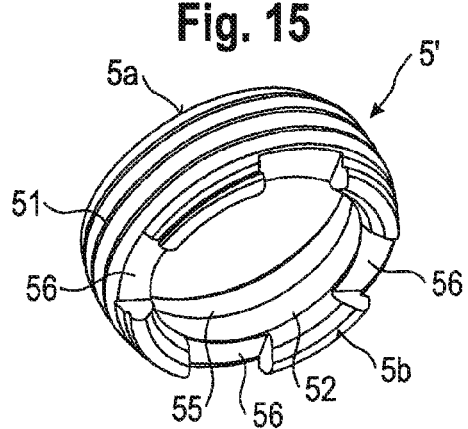
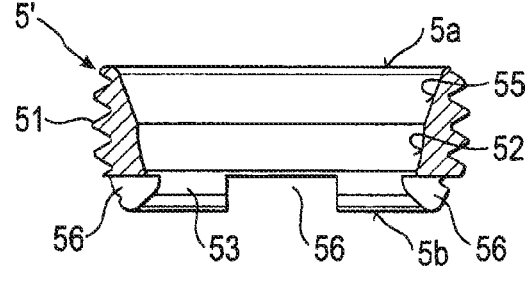

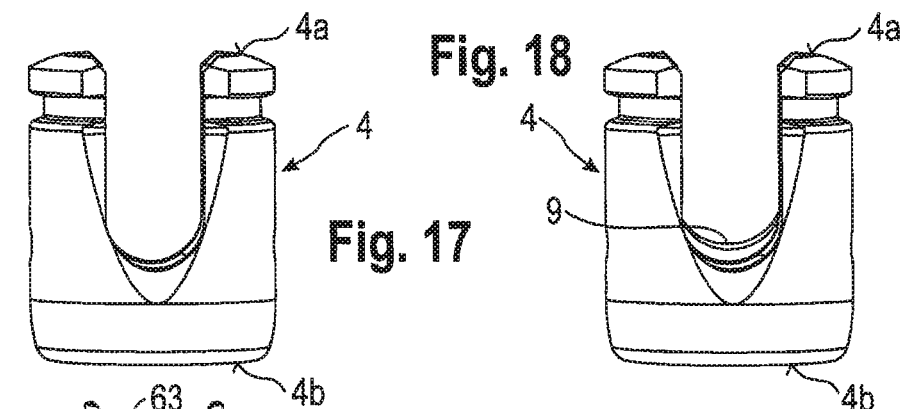
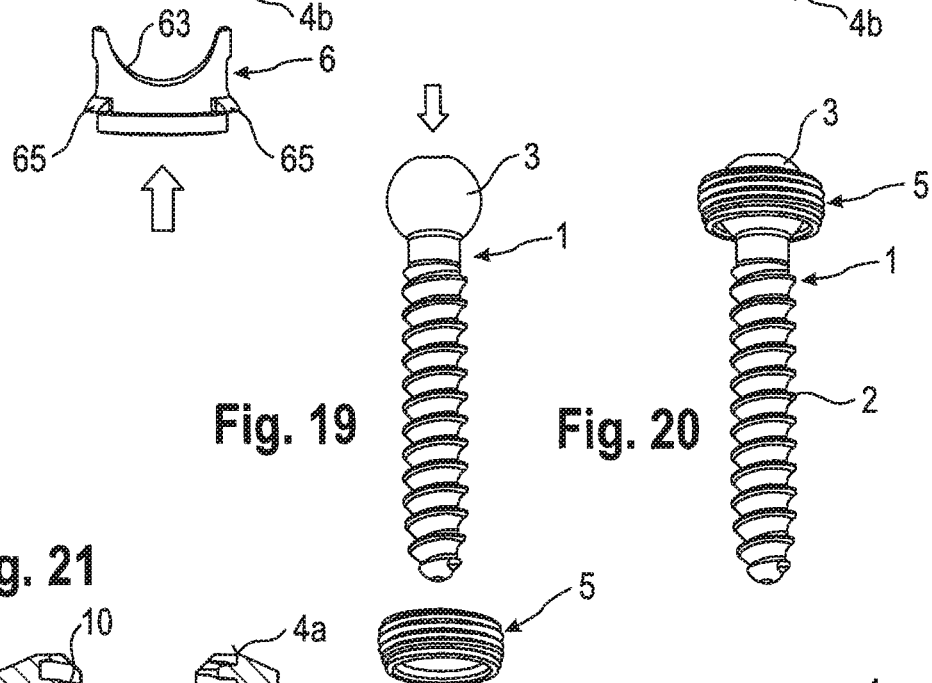
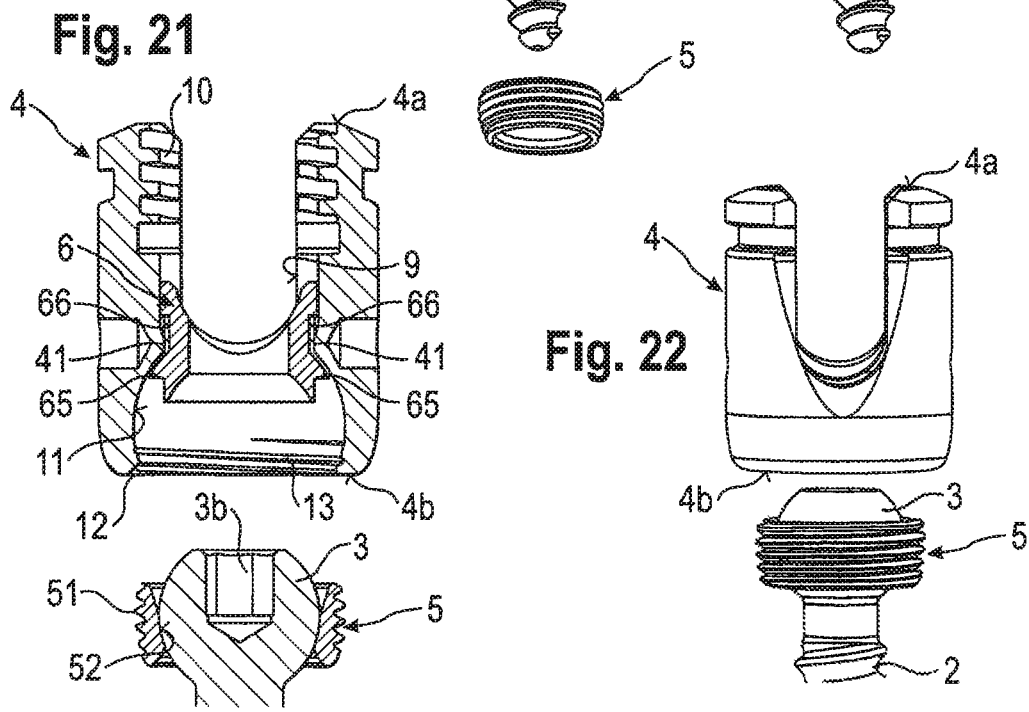

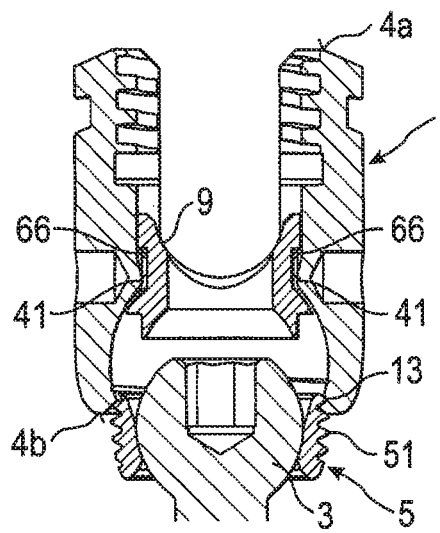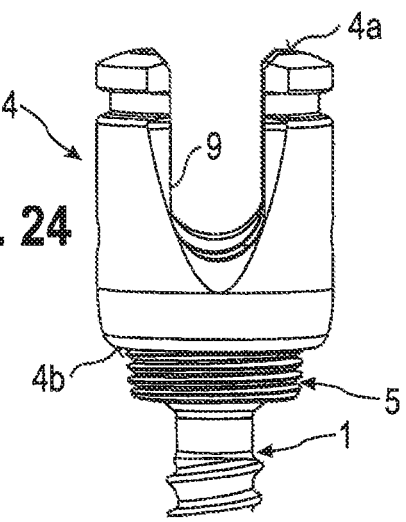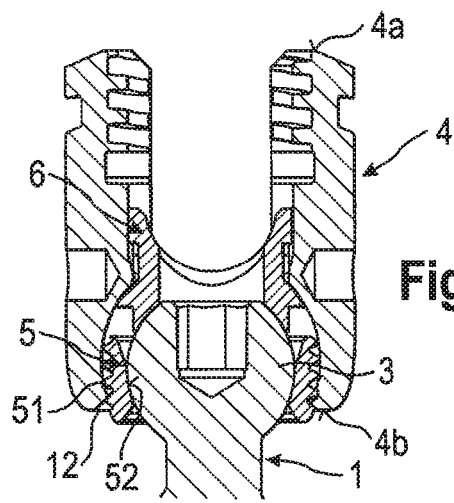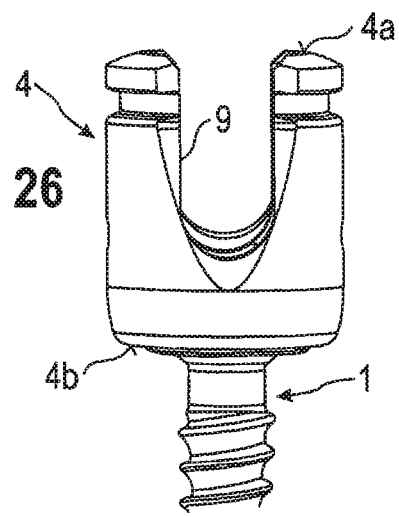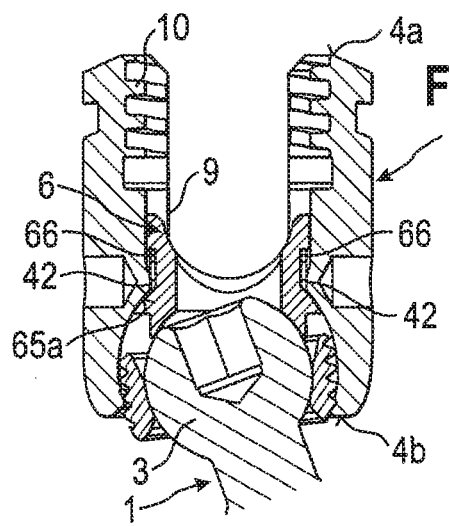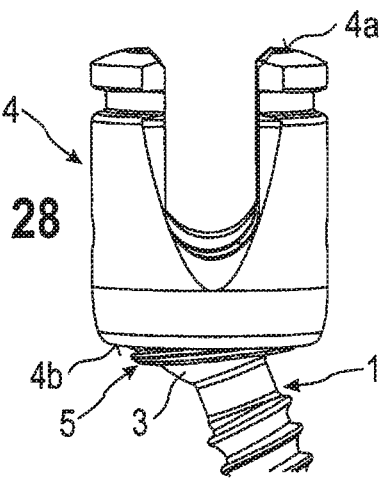

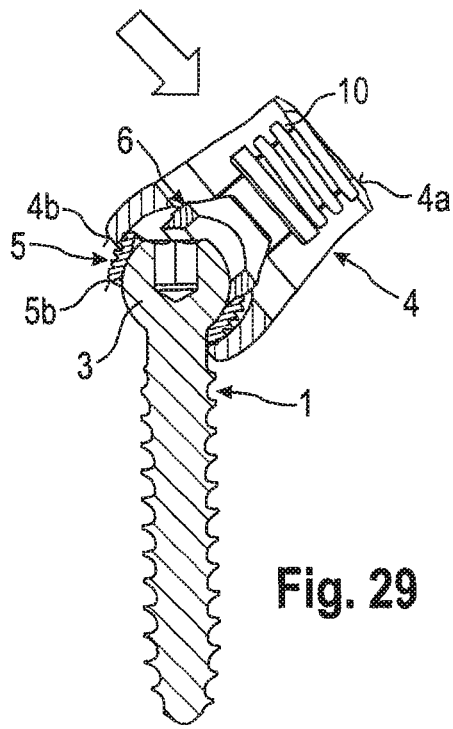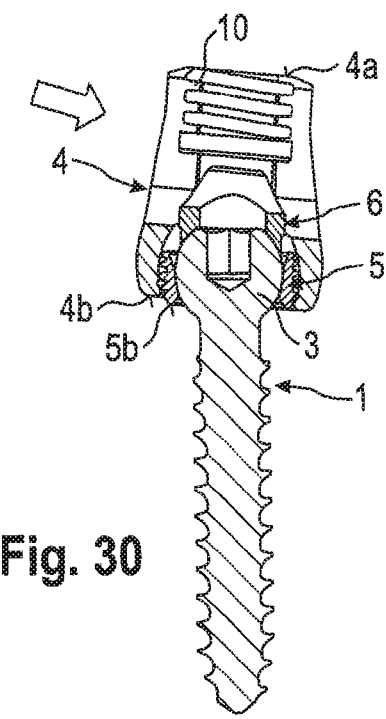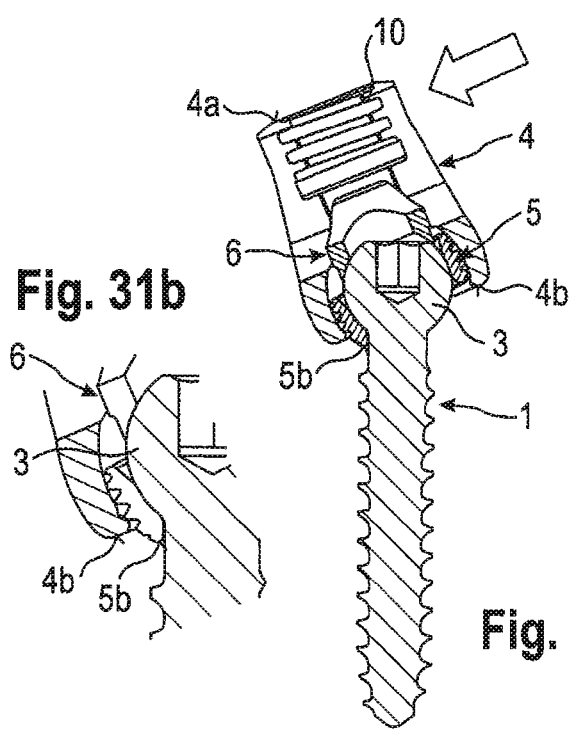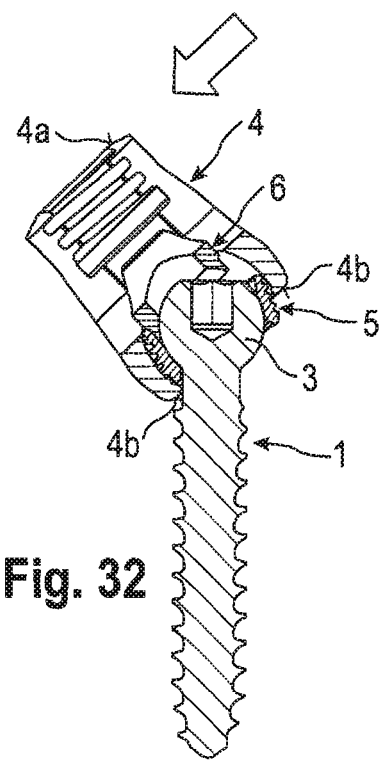

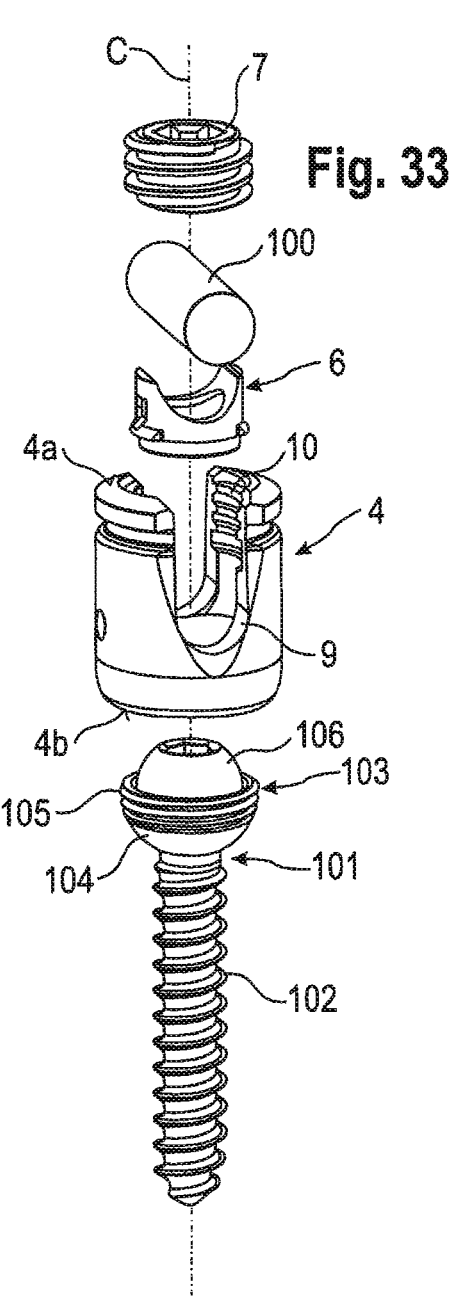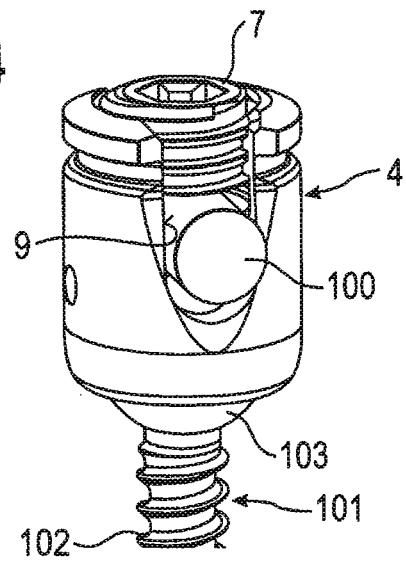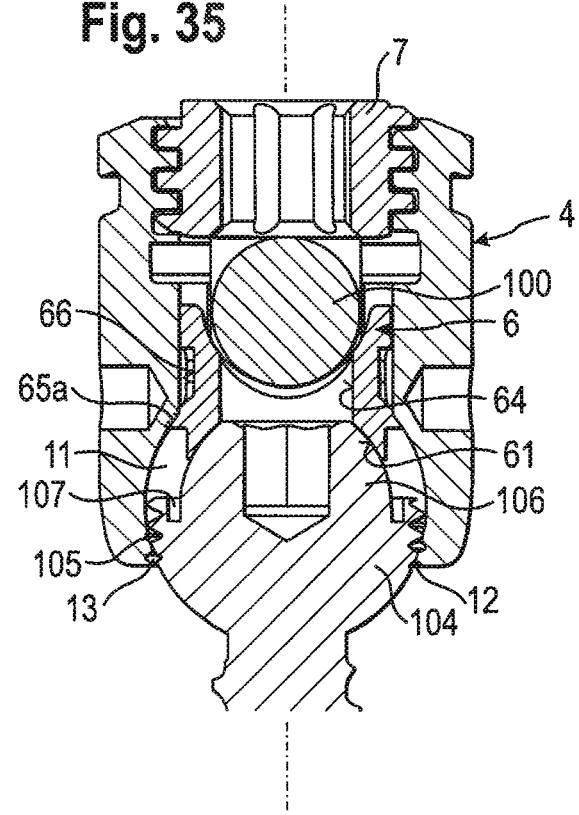

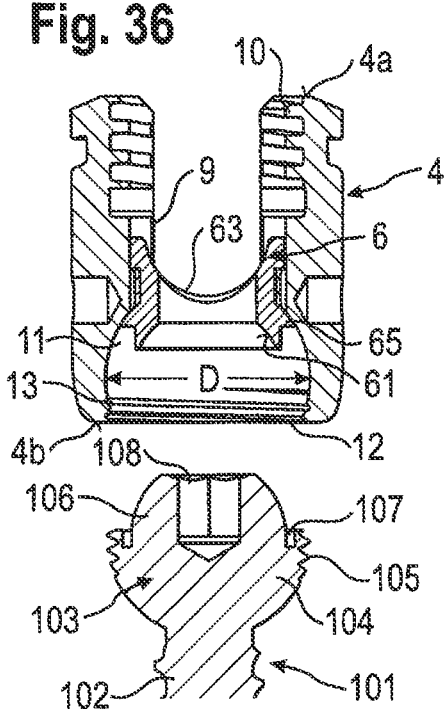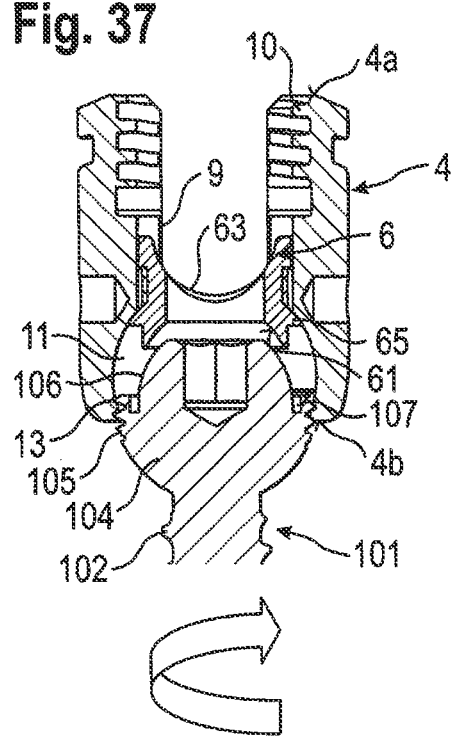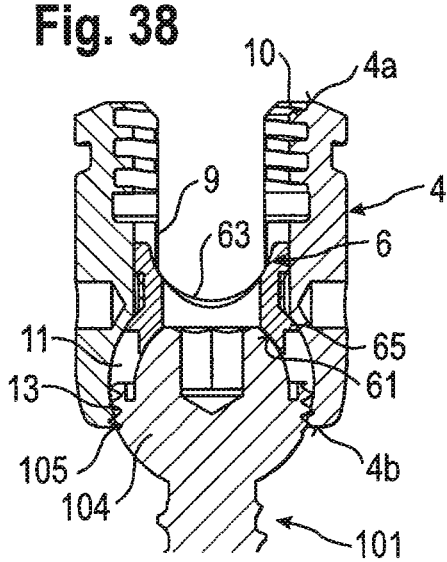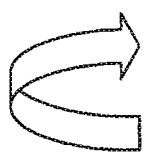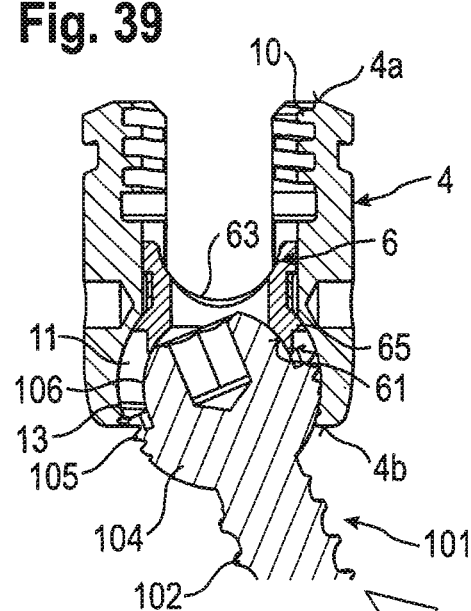

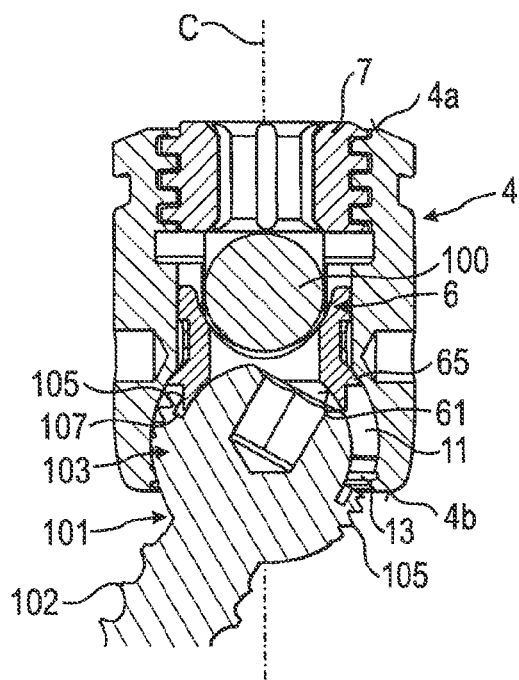
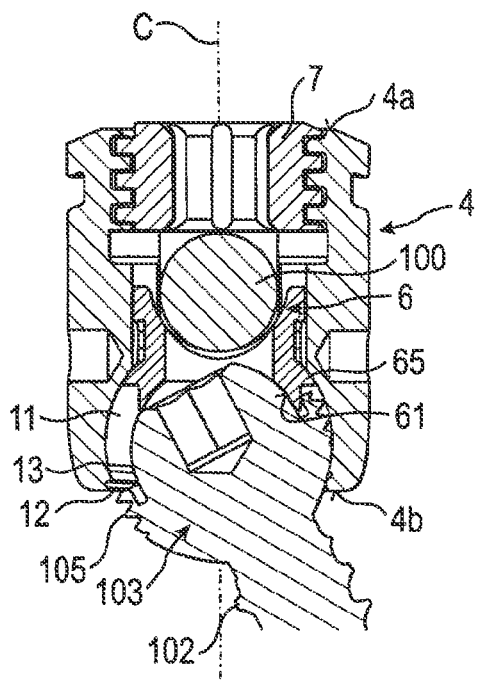
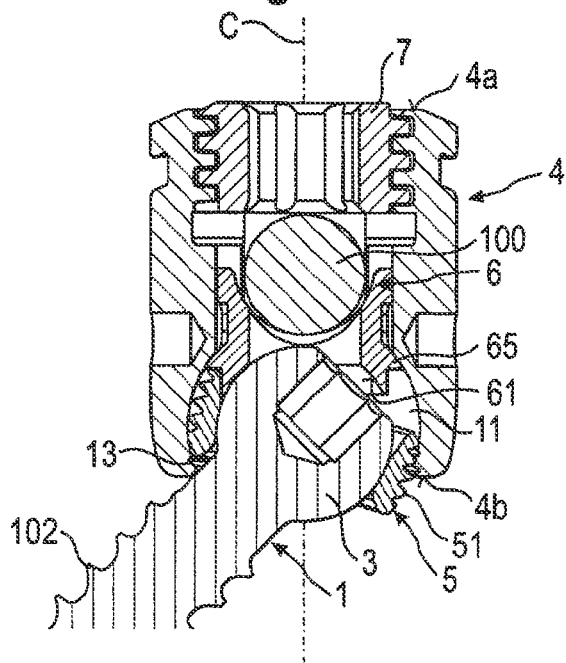
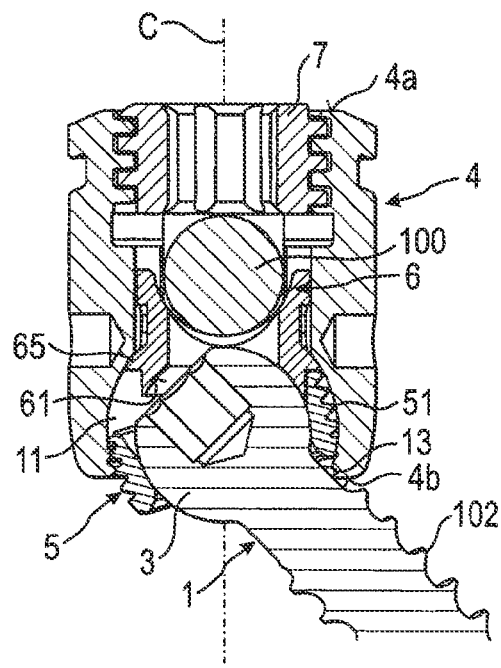

POLYAXIAL BONE ANCHORING SYSTEM

CROSS-REFERENCE TO RELATED APPLICATION(S)

The present application claims the benefit of U.S. Provisional Patent Application Ser. No. 61/525,097, filed Aug. 18, 2011, the contents of which are hereby incorporated by reference in their entirety, and claims priority to European Patent Application EP 11 178 037.5, filed Aug. 18, 2011 the contents of which are hereby incorporated by reference in their entirety.

BACKGROUND

1. Field of the Invention

The invention relates to a polyaxial bone anchoring system including a receiving part and at least a first bone anchoring element and, in some embodiments, a second bone anchoring element that are selectively connectable to the receiving part. Each of the first bone anchoring element and the second bone anchoring element is pivotable in the receiving part and can be fixed at a desired angle. The receiving part couples the bone anchoring element to a stabilization element such as a spinal rod. The first bone anchoring element can be pivoted in the receiving part to an enlarged maximum pivot angle that is greater than a maximum pivot angle of the second bone anchoring element. An orientation of the enlarged pivot angle can be selected within a range of 360° around a central axis of the receiving part, and may be automatically achieved by pivoting the receiving part relative to the bone anchoring element. Such a polyaxial anchoring device is a modular device, wherein the receiving part and the bone anchoring element are connectable by introducing the bone anchoring element from the bottom into the receiving part.

2. Description of Related Art

A polyaxial bone anchoring device with an enlarged pivot angle is described in U.S. Pat. No. 6,736,820. This bone anchoring device includes a bone screw and a receiving part with a seat for the head of the bone screw. The screw member can be pivoted to at least one side by an enlarged angle, because the edge bounding the free end of the receiving part is of asymmetric construction. In a modified embodiment, an insert piece is provided, which has a spherical bottom as a seat for the head of the screw member.

US 2007/0118123 A1 describes a polyaxial bone anchor with increased angulation. The polyaxial bone anchor has a locking element shaped and configured to allow an anchoring member, e.g. a screw or a hook, to polyaxially rotate at large angles about a central axis of the bone anchor before compression locking the anchoring member within an anchor head.

SUMMARY

Although the polyaxial bone anchoring devices described above may provide for enlarged angulation in a desired orientation, there is still a need for an improved polyaxial bone anchoring device in terms of simplicity of the design and variety of applications.

It is an object of embodiments of the invention to provide a polyaxial bone anchoring system that is versatile with respect to its clinical applications and that has a simple design and can be easily assembled, while providing high efficiency of fixation.

A polyaxial bone anchoring system according to an embodiment of the invention includes a bottom loading polyaxial bone anchoring device, wherein an anchoring element can be inserted into a receiving part from a bottom of the receiving part. The system may include at least two anchoring elements to choose from. The polyaxial bone anchoring system can be delivered by the manufacturer as a pre-assembled receiving part with a pressure member and, separate therefrom, bone anchoring elements for different applications, for example, applications that need larger pivot angles and other applications that require reduced pivot angles in comparison to said larger pivot angles. The large pivot angle bone anchoring elements can be provided with pre-assembled or separate sleeve-like insert pieces. The polyaxial bone anchoring device can be assembled at any place and by anybody, in particular by a surgeon or any personnel assisting him or her before or during surgery. Various shanks with different diameters, thread forms, or other features can be combined with a receiving part according to the actual clinical requirements in a particular clinical situation. This gives the surgeon a more flexible and versatile choice of implant combinations, while reducing the number of parts or pieces per set.

Due to the modularity, costs for stock-holding can be decreased.

The polyaxial bone anchoring system has fewer parts, each of which are of simple design. Therefore, the bone anchoring system is cost-effective to manufacture. It provides safe fixation, since the pressure to lock the angular position of the anchoring element with respect to the receiving part is applied effectively only in an axial direction. This enables design of the bone anchoring device to have smaller dimensions and a low profile structure. The bone anchoring device may be devoid of any flexible parts or portions. Therefore, the device may be more reliable, even if during adjustment of an angular position, an orientation of the enlarged pivot angle is changed several times.

A maximum pivot angle provided by the large pivot angle bone anchoring elements relative to the receiving part may be equal to or greater than 45°, measured from a straight position. This renders the bone anchoring device particularly suitable for applications of lateral mass fixation, for example, in the cervical spine. Meanwhile, a maximum pivot angle provided by the reduced pivot angle bone anchoring elements relative to the receiving part may be less than or equal to 30° measured from the straight position, or simply less than the maximum pivot angle provided by the large pivot angle bone anchoring elements.

A locking mechanism for locking the anchoring element, and the sleeve-like insert piece if applicable, provides a high clamping force on a small surface. Therefore, the locking mechanism is efficient, even in small dimensioned low profile elements and structures.

Although for the polyaxial bone anchoring devices with the large pivot angle, an insert member is arranged in a lower portion of the receiving part requiring space for placement, an upper portion of the receiving part can have a small size.

BRIEF DESCRIPTION OF THE DRAWINGS

Further features and advantages of the invention will become apparent from the description of embodiments by means of the accompanying drawings. In the drawings:

FIG. 1 shows a perspective exploded view of a polyaxial bone anchoring device with a spinal rod and a bone anchoring element that facilitates a larger pivot angle according to an embodiment of the invention;

FIG. 2 shows a perspective view of the bone anchoring device of FIG. 1 in an assembled state;

FIG. 11 shows a perspective view of a pressure member of the polyaxial bone anchoring device according to an embodiment;

FIG. 12 shows a side view of the pressure member of FIG. 11 perpendicular to the rod axis;

FIG. 13 shows a side view of the pressure member of FIG. 11 along to the rod axis;

FIG. 14 shows a top view of the pressure element of FIG. 11;

FIG. 15 shows a perspective view from a bottom of another embodiment of a sleeve-like insert piece;

FIG. 16 shows a cross-sectional view of the sleeve-like insert piece of FIG. 15;

FIGS. 17 to 28 show steps of assembling the polyaxial bone anchoring device according to an embodiment;

FIGS. 29 to 32 show steps of adjusting an angle of the bone anchoring element with respect to the receiving part of the polyaxial bone anchoring device according to an embodiment;

FIG. 33 shows a perspective exploded view of a polyaxial bone anchoring device with a spinal rod and a bone anchoring element that facilitates a reduced pivot angle according to an embodiment of the invention;

FIG. 34 shows a perspective view of the bone anchoring device of FIG. 33 in an assembled state;

FIG. 35 shows a cross-sectional view of the bone anchoring device of FIG. 34, the section taken perpendicular to an axis of the rod;

FIGS. 36 to 39 show steps of mounting the bone anchoring element to the receiving part and of pivoting the bone anchoring element according to the embodiment in FIG. 33;

FIGS. 41 and 42 show sectional views, the section taken perpendicular to the rod axis, of a maximum pivot angle achieved with a bone anchoring device with the bone anchoring element that facilitates a reduced pivot angle according to an embodiment;

FIGS. 43 and 44 show cross-sectional views, the section taken perpendicular to the rod axis of a maximum pivot angle achieved with a bone anchoring device with the bone anchoring element that facilitates a larger pivot angle according to an embodiment;

DETAILED DESCRIPTION

Figure 3:
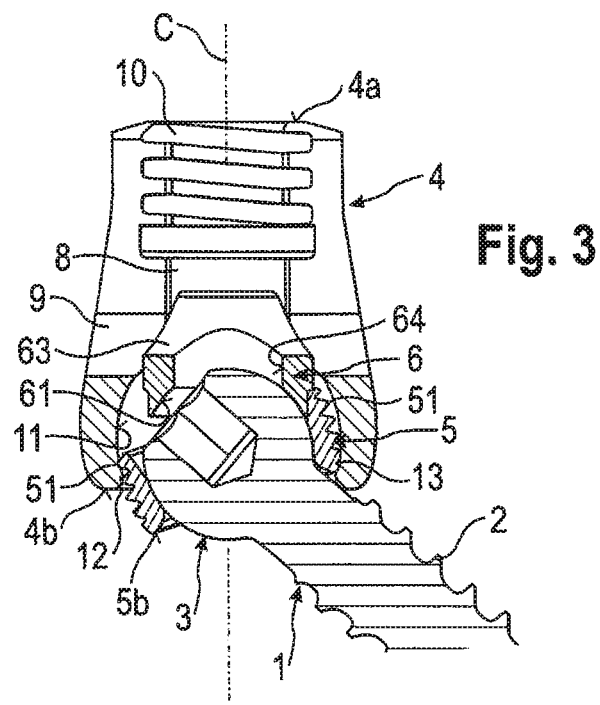
FIG. 3 shows a cross-sectional view of the bone anchoring device of FIGS. 1 and 2 in the assembled state without rod and fixation screw, the section taken along an axis of the rod.

Embodiments of a polyaxial bone anchoring device with a large pivot angle using a bone anchoring element that is part of a polyaxial bone anchoring system will be described with reference to FIGS. 1 to 32.

As shown in FIGS. 1 to 4, a polyaxial bone anchoring device according to a first embodiment includes a bone anchoring element 1 in the form of a bone screw having a threaded shank 2 and a head 3. The head 3 typically has a spherically-shaped outer surface portion 3a and a recess 3b at its free end for engagement with a driver. The head 3 is held in a receiving part 4 that couples the bone anchoring element 1 to a stabilization rod 100. A sleeve-like insert piece 5 providing a seat for the head 3 and a pressure member 6 for exerting pressure onto the head 3 are positionable in the receiving part 4. Furthermore, a fixation element in the form of a fixation screw 7 is provided for securing and fixing the rod 100 in the receiving part 4.

The receiving part 4 has a top end 4a and a bottom end 4b, an axis C defining a central axis of the polyaxial bone anchoring device, and a coaxial bore 8 extending from the top end 4a in the direction of the bottom end 4b. Adjacent to the top end 4a, a substantially U-shaped recess 9 is provided that forms a channel for receiving the rod 100. By means of the recess 9, two free legs are formed which are provided with an internal thread 10 that cooperates with the fixation screw 7.

The coaxial bore 8 opens into an accommodation space 11 provided in the lower part of the receiving part 4. The accommodation space 11 has a lower opening 12 at the bottom end 4b of the receiving part 4 and is shaped as a portion of a hollow sphere including a largest inner diameter D. By the accommodation space 11, a seat for the sleeve-like insert piece 5 is provided such that the seat and the sleeve-like insert piece 5 form a ball and socket joint. It should be noted that the seat can also be tapered or can have any other shape that can be used to realize a ball and socket joint. An inner diameter of the lower opening 12 is slightly smaller than the largest inner diameter D of the accommodation space 11.

Adjacent the opening 12, the receiving part 4 includes a threaded portion 13 with an internal thread. The height of the threaded portion 13 is such that it includes only a few thread turns, for example, at least one thread turn and, at a maximum, just so many thread turns that the sleeve-like insert piece 5 can still freely pivot in the accommodation space once having passed the threaded portion 13 during insertion. In any case, the threaded portion 13 extends to a distance from the portion of the accommodation space 11 having the largest inner diameter D.

It shall be further noted, that an inner diameter of the coaxial bore 8 does not need to be constant between the top end 4a and the accommodation space 11. The coaxial bore 8 may have different portions with different diameters.

The sleeve-like insert piece 5 will be explained with reference to FIGS. 3, 4, and 7 to 10. The sleeve-like insert piece 5 has an upper edge 5a and a lower edge 5b. Between the upper edge 5a and the lower edge, 5b a threaded outer surface portion 51 is provided. The thread corresponds to the thread of the threaded portion 13 of the receiving part 4. Furthermore, the threaded outer surface portion 51 is spherically-shaped. The dimension of the threaded outer surface portion 51 is such that the sleeve-like insert piece 5 is insertable through the opening 12 by screwing, and once the insert piece 5 has passed the threaded portion 13, the sleeve-like insert piece 5 can pivot and rotate in the receiving part 4 when it is positioned in the seat provided by the accommodation space 11. The outer surface of the insert piece 5 can also be only partially threaded, with the threaded portion 51 including or at the portion of the insert piece with the largest diameter.

The sleeve-like insert piece 5 is hollow and includes a central portion 52 that is spherically-shaped with a radius corresponding to the radius of the spherically-shaped outer surface portion 3a of the head 3 of the anchoring element 1. A lower end of the central portion 52 forms a shoulder 53. An inner diameter of the shoulder 53 is smaller than the largest outer diameter of the spherical head 3, such that the head 3 can rotate and pivot in the central spherical portion 52 of the sleeve-like insert piece 5 similar to a ball and socket joint. Between the shoulder 53 and the lower edge 5b, a tapered portion 54 can be provided that tapers outward to allow angulation of the bone anchoring element 1 until the shank 2 comes into contact with the lower edge 5b. Between the spherical central portion 52 and the upper edge 5a, a tapered portion 55 is provided that tapers outwards. An inner diameter of the tapered portion and of a transition between the tapered portion 55 and the spherical central portion 52 may be greater than the largest outer diameter of the head 3, so that the head 3 can be inserted from the upper edge 5a.

Figure 4:
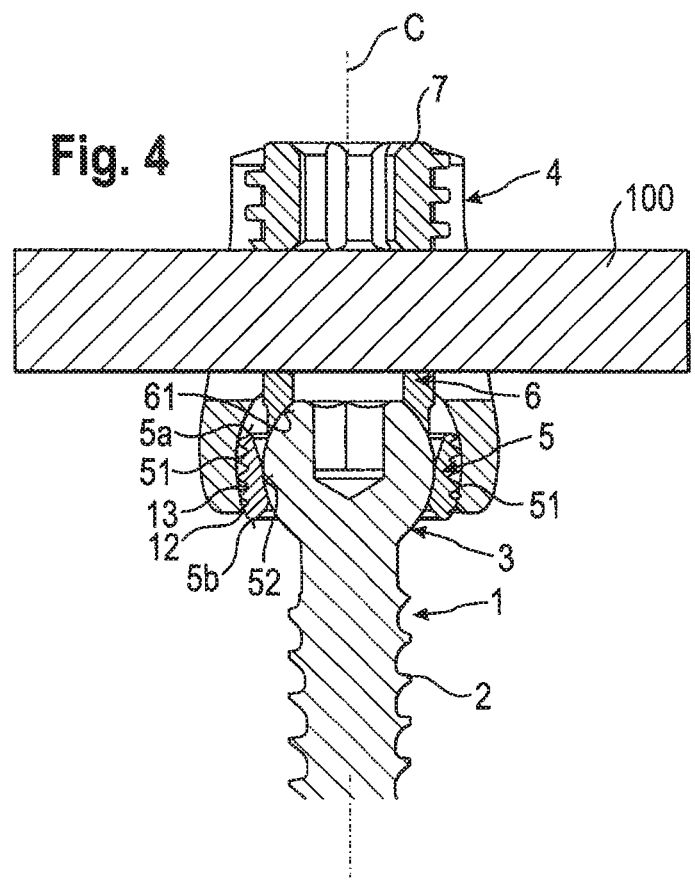
FIG. 4 shows a cross-sectional view of the bone anchoring device of FIGS. 1 and 2 in the assembled state with inserted rod and fixation screw, the section taken along the rod axis.
Figure 5:
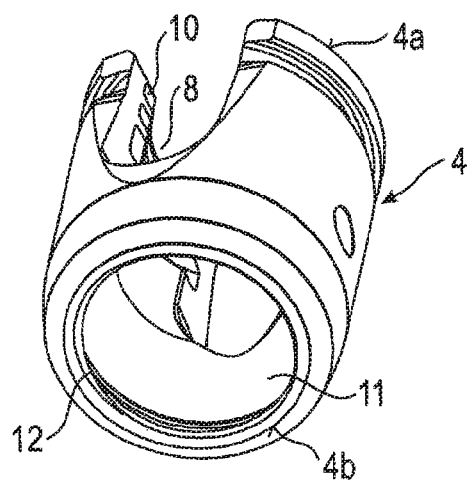
FIG. 5 shows a perspective view from a bottom of the receiving part of the bone anchoring device according to FIGS. 1 to 4.
Figure 6:
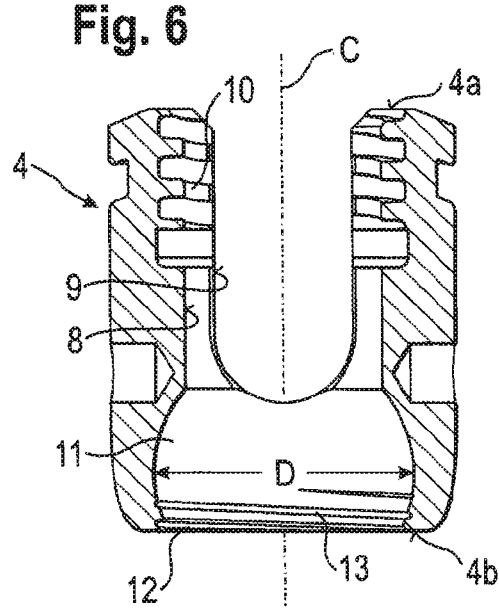
FIG. 6 shows a cross-sectional view of the receiving part of FIG. 5, the section taken perpendicular to the rod axis.
Figure 7:
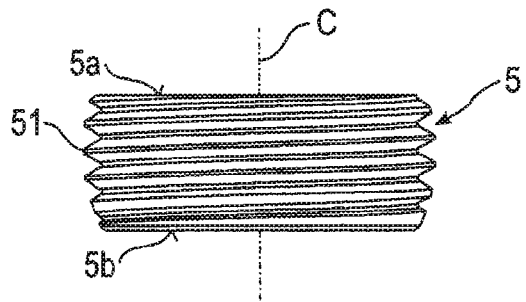
FIG. 7 shows a side view of a sleeve-like insert piece according to a first embodiment.
Figure 8:
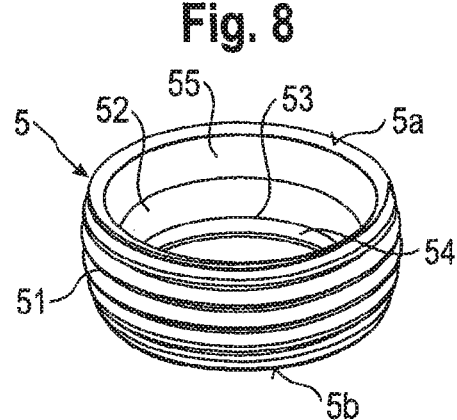
FIG. 8 shows a perspective view from above of the sleeve-like insert piece of FIG. 7.
Figure 9:
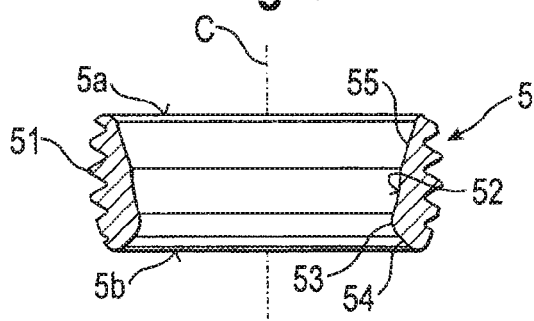
FIG. 9 shows a cross-sectional view of the sleeve-like insert piece of FIGS. 7 and 8, the section taken in a plane containing a central axis of the insert piece.
Figure 10:
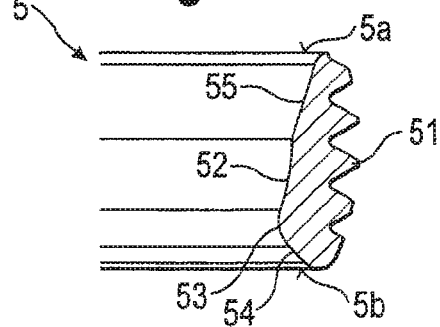
FIG. 10 shows an enlarged portion of FIG. 9.

Spherical center points of the spherical central portion 52 and of the outer spherical portion 51 may be offset from one another in such a way that a center point of the central spherical portion 52 is shifted towards the lower edge 5b. By means of this, a range of angulation for the bone anchoring element 1 can be further increased. A height of the sleeve-like insert piece 5 in an axial direction along the central axis C is less than a height of the head 3 in the axial direction, such that when the head 3 is inserted into the sleeve-like insert piece 5, a portion of the spherical outer surface 3a of the head 3 projects from the upper edge 5a of the sleeve-like insert piece 5 as shown in FIGS. 3 and 4. The inner diameter of the central spherical portion 52 may be dimensioned such that the head 3 can hold the sleeve-like insert piece 5 by a slight tension caused by a friction fit. By means of this, a torque necessary for screwing-in of the anchoring element 1 with the sleeve-like insert piece 5 can be transferred from the anchoring element 1 to the sleeve-like insert piece 5.

In some embodiments, the sleeve-like insert piece 5 is rigid, i.e., does not have any flexible portions such as, for example, slits that would render it flexible.

The pressure member 6 is shown in particular in FIGS. 3, 4, and 11 to 14. The pressure member 6 is substantially cylindrical, with an outer diameter that allows it to move within the coaxial bore 8 and the accommodation space 11. The pressure member 6 has an upper end 6a and a lower edge 6b. Adjacent its lower edge 6b, a spherical recess 61 with a spherical shape that matches the spherical shape of the outer spherical surface portion 3a of the head 3 is provided.

At the upper end 6a, the pressure member 6 has a cylindrical recess 63 for receiving the rod 100 therein. Furthermore, the pressure member 6 has a coaxial bore 64 for allowing access to the head 3 of the anchoring element 1 with a tool. The coaxial bore 64 is also configured to allow a portion of the head 3 to extend therethrough, when the bone anchoring element is in a pivoted condition, as shown, for example, in FIG. 3. The height of the pressure member 6 in an axial direction along the central axis C is such that when the fixation screw 7 is tightened, it presses onto the rod 100, which presses onto the pressure member 6, which in turn acts onto the head 3 of the bone anchoring element 1.

At an outer surface of the pressure member 6, two outwardly extending projections 65 that extend over a length of the pressure member 6 in a circumferential direction, are provided. Each projection 65 has an upper surface 65a, facing the upper end 6a with a spherical shape matching the hollow spherical shape of the accommodation space 11. The projections 65 are offset by 180° and located at positions or are aligned in a direction perpendicular to a rod axis L as shown, for example, in FIG. 13. The projections 65a are located at a distance from the lower edge 6b and at a distance from a bottom of the cylindrical recess 63 along a direction of the central axis C. Above the projections 65, two recesses 66 are provided, offset from each other by 180°. The recesses have a portion 66a extending into the spherical upper surfaces 65a of the projections 65. The recesses 66 serve as a space for taking-up material of the inner wall of the receiving part generated by crimping, as explained below.

A further embodiment of a sleeve-like insert piece 5' is shown in FIGS. 15 and 16. The sleeve-like insert piece 5' according to FIGS. 15 and 16 differs from the sleeve-like insert piece 5 described above by the additional provision of a drive feature for engagement with a tool to screw the sleeve-like insert piece 5' into the receiving part 4. All other portions are the same as in the first embodiment and are indicated by the same reference numerals, and as such, the descriptions thereof will not be repeated. The sleeve-like insert piece 5' has at its lower edge 5b slits 56 that serve as an engagement portion for a tool. The slits 56 can have any shape that allows engagement with a tool. A plurality of slits 56 may be provided in a circumferential direction. If the sleeve-like insert piece 5' is used, the head 3 does not need to be clamped in the sleeve-like insert piece 5'.

The bone anchoring device, as a whole or in part, is made of a bio-compatible material, such as a bio-compatible metal, for example titanium or stainless steel, of a bio-compatible alloy, such as nickel-titanium alloys, for example, Nitinol, or of bio-compatible plastic materials, such as, for example, polyetheretherketone (PEEK).

Steps of assembling the bone anchoring device will be explained with reference to FIGS. 17 to 28. FIG. 17 shows a side view of a first step of assembling the bone anchoring device. The pressure member 6 is introduced into the receiving part 4 through the lower opening 12 until cylindrical recess 63, as shown in FIG. 18, projects slightly above the U-shaped recess 9 of the receiving part 4, and is aligned therewith. As shown in the sectional view according to FIG. 21, the pressure member 6 may be mounted to or held in the receiving part 4 by crimping, wherein with a crimping tool the inner wall of the receiving part 4 is slightly deformed to form deformed portions 41 protruding into the recesses 66. As the recesses 66 are larger in axial direction than the deformed portions 41, the pressure member 6 can move slightly within the receiving part 4 in an axial direction. The receiving part 4 and the pressure member 6 may be pre-assembled and delivered in such a pre-assembled state.

The sleeve-like insert piece 5 is mounted to the bone anchoring element 1, as shown in a side view in FIGS. 19 and 20. The bone anchoring element 1 is introduced from the upper edge 5a into the sleeve-like insert piece 5 until the spherical head 3 rests in the spherically-shaped central portion 52, and is slightly clamped therein in some embodiments. A large variety of bone anchoring elements each with or without a mounted sleeve-like insert piece, may be provided.

As can be seen in FIGS. 21 to 24, the bone anchoring element 1 with mounted sleeve-like insert piece 5 is introduced from the bottom end 4b into the receiving part 4. FIG. 21 shows a cross-sectional view of the polyaxial bone anchoring device with the section taken perpendicular to the rod axis. FIG. 22 shows a side view of the polyaxial bone anchoring device before assembling the bone anchoring element 1 with the receiving part 4. FIG. 23 shows a cross-sectional view of the bone anchoring device and FIG. 24 a side view thereof, wherein the bone anchoring element 1 is introduced into the receiving part 4 through the lower opening 12. The thread of the outer surface portion 51 of the sleeve-like insert piece 5 engages the threaded portion 13 of the receiving part 4. Because the sleeve-like insert piece 5 is slightly clamped onto the head 3 of the bone anchoring element 1, the torque applied to the shank 2 is transferred to the insert piece 5 to engage the threaded portion 13. When the sleeve-like insert piece 5' is used, a tool may be used to screw in the anchoring element 1 with the sleeve-like insert piece 5'.

FIGS. 25 and 26 show a cross-sectional view and a corresponding side view of the polyaxial bone anchoring device, wherein the bone anchoring element 1 and the sleeve-like insert piece 5 have been completely inserted. In this position, the pressure member 6 is at its uppermost position, in which the upper spherical portions 65a of the projections 65 abut against the inner wall of the accommodation space 11. The head 3 of the anchoring element 1 and the sleeve-like insert piece 5 are pivotable in the receiving part 4.

The assembly steps shown in FIGS. 19 to 26 can be performed by any person at any place. Therefore, a suitable polyaxial bone anchoring device can be selected from a great variety of bone anchoring elements that can be assembled with receiving parts on demand.

In a final step shown in FIGS. 27 and 28, wherein FIG. 27 shows a cross-sectional view and FIG. 28 a corresponding side view of the polyaxial bone anchoring device, the pressure member 6 is further fixed by crimping. Through further crimping, the pressure member 6 can be moved downward until it slightly presses onto the head 3 of anchoring element 1 with spherical recess 61. By this additional crimping step, deformed portions 42 are generated that hold the pressure member 6 in a predetermined preliminary position. By adjusting the force of the crimping operation, a defined friction fit is achieved between the head 3 and the pressure member 6. The bone anchoring element can then be pivoted only by overcoming the frictional force between the pressure member 6 and the head 3.

The assembly of the bone anchoring element 1 and the receiving part 4 with the second embodiment of the sleeve-like insert piece 5' is carried out in the same manner as the first embodiment, except that a tool is used for engaging the slits 56 and rotating the sleeve-like insert piece 5'.

The steps of use of the bone anchoring device are shown by the cross-sectional views of FIGS. 29 to 32. The fixation screw and the rod are omitted in these exemplary figures. First, the anchoring element 1 is inserted in a bone part or in a vertebra. Usually, several bone anchoring devices are needed to fix a stabilization rod 100 to the bone parts or the vertebrae to be stabilized. After the bone anchoring elements 1 are inserted, one example of which is shown in FIGS. 29 to 32, the receiving part 4 is adjusted by pivoting and/or rotating in order to be able to insert the stabilization rod 100 into the U-shaped recess 9. In the condition shown in FIGS. 29 to 32, both, the sleeve-like insert piece 5 and the head 3 of the bone anchoring element 1 are independently and freely pivotable. The sleeve-like insert piece 5 is rotatable and pivotable in the receiving part 4, and both are rotatable and pivotable with respect to the head 3 of the bone anchoring element 1. The sleeve-like insert piece 5 provides for an enlarged range of angulation compared to embodiments where the head 3 is directly received in the receiving part 5, because the distance between the shank 2 and the lower end 4b of the receiving part 4 is greater. Because the sleeve-like insert piece 5 is rotatable and pivotable within the receiving part 4, an enlarged range of angulation can be achieved at any position of the receiving part 4 with respect to the bone anchoring element 1 for 360° around the central axis C of the receiving part 4. As shown in FIG. 30, pivoting the receiving part 4 towards an opposite direction may also pivot the sleeve-like insert piece 5.

As shown in FIG. 31a and in the enlarged representation of FIG. 31b, further pivoting the receiving part 4 may in some instances essentially maintain a position of the sleeve-like insert piece 5. As soon as the shank 2 of the bone anchoring element 1 comes into contact with the lower edge 5b of the sleeve-like insert piece as shown in FIGS. 31a and 31b, the sleeve-like insert piece 5 will also be pivoted. The shank 2 pushes the insert piece 5 until the shank 2 abuts against an edge of the lower opening 12 of the receiving part 4, as shown in FIG. 32. Hence, in FIG. 32, the receiving part 4 is pivoted at a maximum pivot angle with respect to the bone anchoring element 1. The maximum pivot angle to be achieved depends on the dimensions of the sleeve-like insert piece 5, the receiving part 4, and the bone anchoring element 1, but is typically equal to or greater than 45° measured from a straight or zero angle position.

While in FIGS. 29 to 32 an example is shown in which pivoting is carried out in a plane that contains the rod axis, it should be noted, that the same steps can be carried out at any other direction for 360° around the central axis C of the receiving part 4.

The sleeve-like insert piece 5 together with the bone anchoring element 1 cannot escape from the lower opening 12 because of the obstacle provided by the threaded portion 13. The friction fit between the pressure member 6 and the head 3 of the anchoring element 1 has the effect that the receiving part 4 can be maintained provisionally at any position with respect to the bone anchoring element 1.

Finally, the rod 100 is inserted and the inner screw 7 is tightened to press the pressure element 6 onto the head 3, to lock the head 3 and the sleeve-like insert piece 5 simultaneously.

Embodiments of a polyaxial bone anchoring device with a reduced pivot angle relative to the device in FIGS. 1 to 32, using a bone anchoring element that is part of a polyaxial bone anchoring system will be described with reference to FIGS. 33 to 39.

The bone anchoring device shown in FIGS. 33 to 39 differs from the bone anchoring device shown in FIGS. 1 to 32 in the designs of the bone anchoring elements. The receiving part 4, the pressure member 6, and the inner screw 7 are the same as or similar to those in the previous figures and embodiments, so that the descriptions thereof will not be repeated.

The bone anchoring element 101 has a threaded shank 102 and a head 103. The head 103 has a first portion 104 adjacent the threaded shank 102 that is shaped substantially as a hemisphere, with increasing diameter away from the threaded shank 102. At an end of the hemisphere facing away from the threaded shank 102, a threaded outer surface portion 105 is provided. An outer diameter of the portion 105 matches with the inner diameter of the threaded portion 13 at the lower portion of the receiving part 4. In other words, the outer diameter of the threaded outer surface portion 105 of the head 103 corresponds substantially to the outer diameter of the sleeve-like insert piece 5, 5' of the bone anchoring element 1 of the previous embodiments. The head 103 further comprises a second portion 106 which is threadless and spherically-shaped with increasing diameter in a direction towards the shank 102. The diameter of the second portion 106 is smaller than that of the first portion 104 and substantially corresponds to the inner diameter of the spherical recess 61 of the pressure member 6. The head 103 further has at its free end opposite to the shank 102 a recess 108 for engagement with a tool. Between the first portion 104 and the second portion 106, a circumferential groove 107 is provided that serves for engagement by the lower edge 6b of the pressure member 6.

Also the second anchoring element 101 can have different types of shanks, for example, with respect to the length, the diameter, and the design of the shank.

The bone anchoring element 101 is mounted to the receiving part 4 from the bottom end 4b. As shown in FIGS. 36 and 37, first, the bone anchoring element 101 is moved with its head 103 towards the lower opening 12 until the threaded outer surface portion 105 engages the threaded portion 13 at the lower end 4b of the receiving part 4 (FIG. 37). Then, the bone anchoring element 101 is further screwed to the receiving part 4 while in a zero angle position, as shown in FIG. 38. When the threaded portion 105 of the head 103 has passed the threaded portion 13 of the receiving part 4, the anchoring element 101 can freely pivot in the accommodation space 11, as shown in FIG. 39. Anchoring element 101 cannot fall out of receiving part 4, due to the threaded portion 13 acting as a stop. The pressure member 6 can be positioned such that it exerts a preload or friction force onto the head 103 in order to allow pivoting of the bone anchoring element 101 only by application of a force that overcomes the friction force. When the bone anchoring element 101 is received in the accommodation space 11, the pressure member 6 engages the second portion 106 of the head 103.

Figure 40:
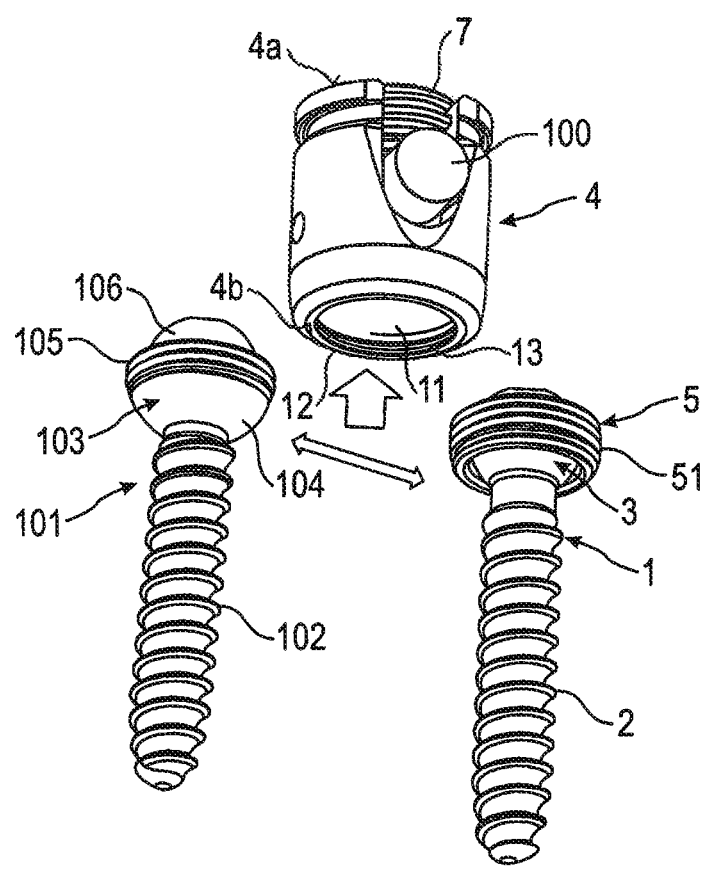
FIG. 40 schematically shows the interchangeability of the bone anchoring elements that facilitate a larger pivot angle and that facilitate a reduced pivot angle with respect to the receiving part with inserted rod in a perspective view according to an embodiment.

As shown in FIG. 40, the bone anchoring element 1 with the sleeve-like insert piece 5 and the bone anchoring element 101 can be selectively connected to the receiving part 4 by insertion through the lower opening 12.

Because the outer dimensions of the first portion 104 of the head 103 of the bone anchoring element 101 fits to the inner dimensions of the threaded portion 13 of the accommodation space 11 of the receiving part 4 in the same or similar manner as the outer dimensions of the sleeve-like insert piece 5, 5' of the first bone anchoring element 1 fit therein, the bone anchoring elements 1, 101 can be used interchangeably. Therefore, one can select whether to implement a bone anchoring device with a large pivot angle using the bone anchoring element 1 with sleeve-like insert piece 5, 5', or to implement a bone anchoring device with a reduced pivot angle using the bone anchoring element 101.

FIG. 41 and FIG. 42 show the bone anchoring device with the bone anchoring element 101 that facilitates a reduced pivot angle, wherein the bone anchoring element 101 is pivoted to a maximum angle towards one side (FIG. 41) and towards an opposite side (FIG. 42). The maximum pivot angle is defined by the condition in which the threaded outer surface portion 105 begins to disengage the threaded portion 13. The pressure member 6 presses onto the head 103, and its lower edge 66 engages the groove 107.

FIG. 43 and FIG. 44 show the bone anchoring device with the bone anchoring element 1 that facilitates an enlarged pivot angle, in a condition in which the bone anchoring element 1 is pivoted to a maximum pivot angle to one side (FIG. 43) and to an opposite side (FIG. 44). The maximum pivot angle is defined when the threaded shank 2 abuts against the bottom end 4b of the receiving part 4. Due to the sleeve-like insert piece 5, the maximum pivot angle for this bone anchoring device is substantially larger than for the bone anchoring device with the bone anchoring element 101 as shown in FIGS. 41 and 42.

Because the parts of the bone anchoring system including the receiving part 4 with the pressure element 6 on the one hand, and the bone anchoring element 1 with the sleeve-like insert piece 5, 5' and the bone anchoring element 101 on the other hand, are easy to assemble, a modular system that provides for a broad range of clinical applications is provided.

Further modifications of the embodiments described are conceivable. For example, for the bone anchoring element, all kinds of anchoring elements can be used and combined with the receiving part. Such anchoring elements may be, for example, screws of different length, with different diameters, cannulated screws, screws with different thread forms, nails, hooks, etc. The head and the shank may also be separate parts that are connectable to each other.

Modifications of the receiving part may include instead of the U-shaped recess, which is perpendicular to the central axis, a recess for the rod which is inclined or open to the side or which is in the form of a closed channel.

Figures 45, 46:
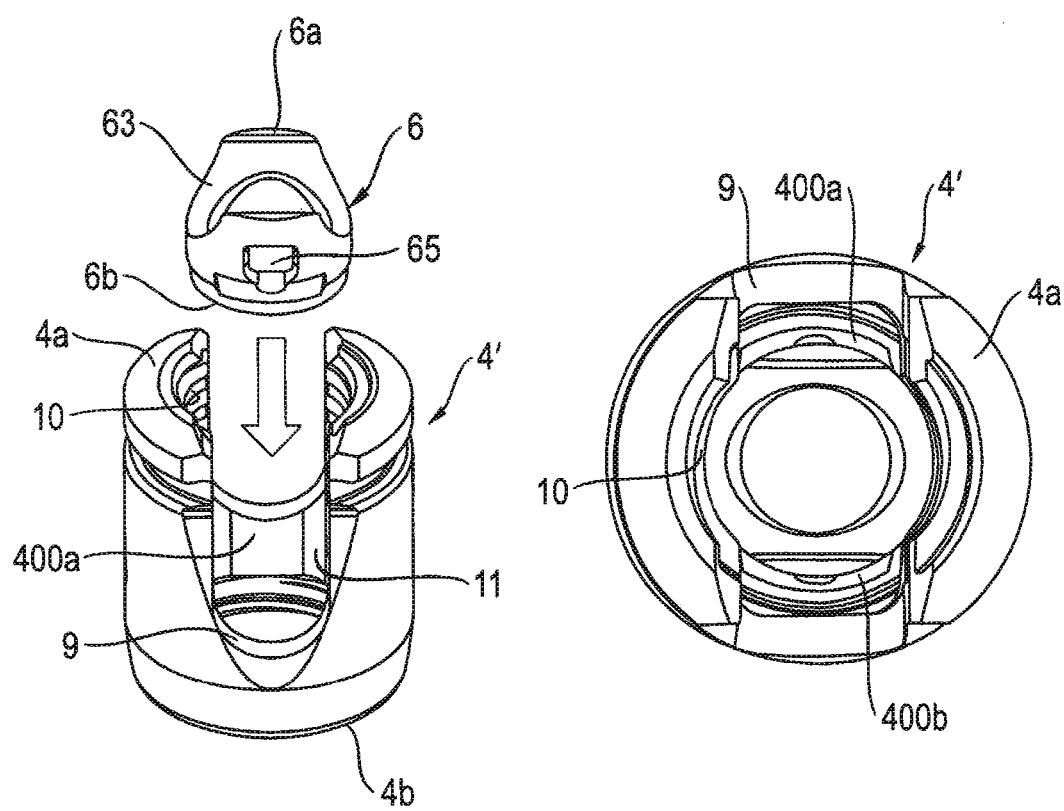
FIG. 45 shows a perspective view of a modified receiving part with pressure ember.
FIG. 46 shows a top view of the modified receiving part of FIG. 45.

In another modified embodiment shown in FIGS. 45 and 46, in order to allow a pressure member 6 to be inserted from a top end 4a of a receiving part 4', the receiving part 4' has two opposed recesses 400a, 400b along inner walls of coaxial bore 8 and accommodation space 11. The recesses 400a, 400b are aligned with U-shaped recess 9, and extend from a bottom of the U-shaped recess 9 into the accommodation space 11. A size of the recesses 400a, 400b is such that the pressure member 6 can be introduced from the top end 4a of the receiving part 4' when projections 65 are positioned in or aligned with the U-shaped recess 9. When the projections 65 enter the accommodation space 11, the pressure member 6 can be rotated, and a recess 63 of the pressure member 6 can be aligned with the U-shaped recess 9 of the receiving part 4'.

Other kinds of locking devices including outer nuts, outer caps, bayonet locking devices, or others are also possible. The locking device can also be a two part locking device having one locking element that locks the head of the anchoring element and another locking element that locks the rod. In some embodiments, the inner surface portion of the pressure member that contacts the head is not necessarily spherically-shaped. The inner surface portion can have any other shape that is suitable to exert pressure onto the head.

The polyaxial bone anchoring system can also be realized generally through any receiving part, a first bone anchoring element that is pivotable in the receiving part to a first maximum pivot angle, and a second bone anchoring element that is pivotable in the receiving part to a second maximum pivot angle, wherein the first maximum pivot angle is larger than the second maximum pivot angle, and wherein the first and the second bone anchoring elements are configured to be interchangeable.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring system comprising:
   a receiving part having a first end and a second end, a central axis extending through the first end and the second end, a transverse channel at the first end for receiving a rod, and an accommodation space having an opening at the second end;
   a first anchoring element having a first shank for anchoring in a bone or a vertebra and a first head having a spherically-shaped outer surface portion;
   a sleeve-like insert piece configured to be arranged around a portion of the first head and to be arranged in and pivot in the accommodation space of the receiving part, such that an angle formed by a central axis of the insert piece with the central axis of the receiving part is adjustable when the insert piece is in the accommodation space;

a second anchoring element having a second shank for anchoring in a bone or a vertebra and a second head having a greater width than a greatest width of the first head, wherein the first head with the insert piece and the second head are each configured to be introduced into the accommodation space through the opening, such that the first bone anchoring element and the second bone anchoring element are configured to be interchangeably connectable to the receiving part; and a pressure member configured to be arranged at least partially in the accommodation space, the pressure member comprising a portion configured to contact the first head or the second head to exert pressure onto the first head or the second head when the pressure member and one of the first head or the second head are arranged in the receiving part;

wherein when any one of the first anchoring element or the second anchoring element is connected to the receiving part, the connected anchoring element is pivotable relative to the receiving part and can be locked at an angle relative to the receiving part by exerting pressure with the pressure member onto the respective head of the connected anchoring element.

2. The polyaxial bone anchoring system of claim 1, wherein the receiving part comprises a first engagement portion near the second end.

3. The polyaxial bone anchoring system of claim 2, wherein the insert piece comprises a second engagement portion for engaging the first engagement portion of the receiving part.

4. The polyaxial bone anchoring system of claim 3, wherein the first engagement portion and the second engagement portion comprise threaded portions.

5. The polyaxial bone anchoring system of claim 3, wherein the insert piece is insertable into the accommodation space through the opening by engaging the first engagement portion and the second engagement portion, and wherein when the insert piece is inserted in the accommodation space and the first engagement portion and the second engagement portion are disengaged, the insert piece is freely pivotable in the accommodation space.

6. The polyaxial bone anchoring system of claim 3, wherein the second engagement portion extends over a full outer surface of the insert piece.

7. The polyaxial bone anchoring system of claim 3, wherein when the insert piece is in the receiving part, the first engagement portion and the second engagement portion form a stop to prevent the insert piece from being removed from the receiving part.

8. The polyaxial bone anchoring system of claim 2, wherein the accommodation space has a portion with a largest diameter, and wherein the first engagement portion extends from the opening to a distance from the largest diameter of the accommodation space.

9. The polyaxial bone anchoring system of claim 2, wherein the second head comprises a second engagement portion for engaging the first engagement portion of the receiving part.

10. The polyaxial bone anchoring system of claim 9, wherein the first engagement portion and the second engagement portion comprise threaded portions.

11. The polyaxial bone anchoring system of claim 9, wherein the second engagement portion is on a first portion of the second head, and wherein the pressure member is configured to act on a second portion of the second head when the second head and the pressure member are in the receiving part.

12. The polyaxial bone anchoring system of claim 11, wherein the first portion is spherically shaped.

13. The polyaxial bone anchoring system of claim 9, wherein when the second head is in the receiving part, the first engagement portion and the second engagement portion form a stop to prevent the second head from being removed from the receiving part.

14. The polyaxial bone anchoring system of claim 1, wherein the insert piece is configured to be held on the first head by friction.

15. The polyaxial bone anchoring system of claim 1, wherein the insert piece has a first edge and a second edge, and wherein an engagement portion is provided at the second edge for engaging a tool.

16. The polyaxial bone anchoring system of claim 1, wherein when the first head with the insert piece are inserted in the receiving part, the first anchoring element and the insert piece are independently pivotable relative to the receiving part when the first shank and an edge of the insert piece are out of contact.

17. The polyaxial bone anchoring system of claim 16, wherein when the first shank engages the edge of the insert piece, the first anchoring element and the insert piece are pivotable together.

18. The polyaxial bone anchoring system of claim 1, wherein the insert piece has an inner spherical surface portion that forms a seat for the first head.

19. The polyaxial bone anchoring system of claim 1, wherein the accommodation space defines a hollow spherically-shaped portion forming a seat for the insert piece or the second head.

20. The polyaxial bone anchoring system of claim 1, wherein when the first head with the insert piece is inserted in the receiving part, the first anchoring element is pivotable to a first maximum pivot angle relative to the receiving part, wherein when the second head is inserted in the receiving part, the second anchoring element is pivotable to a second maximum pivot angle relative to the receiving part, and wherein the second maximum pivot angle is smaller than the first maximum pivot angle.

21. The polyaxial bone anchoring system of claim 1, wherein when any one of the first anchoring element or the second anchoring element is connected to the receiving part, the connected anchoring element is pivotable relative to the receiving part such that the angle formed between the central axis of the receiving part and a longitudinal axis of the connected anchoring element is adjustable.

22. A method of coupling a rod to a bone or vertebra via a polyaxial bone anchoring device, the bone anchoring device assembled from parts of a bone anchoring system comprising a receiving part having a first end and a second end, a central axis extending through the first end and the second end, a transverse channel at the first end for receiving a rod, and an accommodation space having an opening at the second end, a first anchoring element having a first shank for anchoring in a bone or a vertebra and a first head having a spherically-shaped outer surface portion, a sleeve-like insert piece configured to be arranged around a portion of the first head and to be arranged in and pivot in the accommodation space of the receiving part, such that an angle formed by a central axis of the insert piece with the central axis of the receiving part is adjustable when the insert piece is in the accommodation space, a second anchoring element having a second shank for anchoring in a bone or a vertebra and a second head having a greater width than a greatest width of the first head, wherein the first head with the insert piece and the second head are each configured to be introduced into the accommodation space through the opening, such that the first bone anchoring element and the second bone anchoring element are configured to be interchangeably connectable to the receiving part, a pressure member configured to be arranged at least partially in the accommodation space, the pressure member comprising a portion configured to contact the first head or the second head to exert pressure onto the first head or the second head when the pressure member and one of the first head or the second head are arranged in the receiving part, and a fixation element, the method comprising:
- connecting any one of the first anchoring element or the second anchoring element to the receiving part by introducing the first head with the insert piece or the second head through the opening and into the accommodation space of the receiving part;
- inserting the connected anchoring element into a bone or vertebra;
- pivoting the receiving part relative to the connected anchoring element;
- inserting a rod into the channel of the receiving part, wherein the pressure member is arranged between the rod and the connected anchoring element;
- advancing the fixation element in the channel, such that the fixation element exerts pressure on the rod, the rod exerts pressure on the pressure member, and the pressure member exerts pressure onto the respective head of the connected anchoring element, to lock a position of the rod and an angle of the connected anchoring element relative to the receiving part.

23. The method of claim 22, further comprising inserting the pressure member into the receiving part.

24. The method of claim 23, further comprising holding the pressure member at a first position when the one of the first anchoring element or the second anchoring element is connected to the receiving part and the rod is not inserted into the channel, such that the pressure member exerts a frictional force on the head of the connected anchoring element to hold a position of the receiving part relative to the connected anchoring element, wherein said position is adjustable by applying a force greater than the frictional force on the receiving part or the connected anchoring element.

25. The method of claim 22, wherein when the first anchoring element is connected to the receiving part, the first anchoring element is pivotable to a first maximum pivot angle relative to the receiving part, when the second anchoring element is connected to the receiving part, the second anchoring element is pivotable to a second maximum pivot angle relative to the receiving part, and wherein the second maximum pivot angle is smaller than the first maximum pivot angle.

26. The method of claim 22, wherein when the first anchoring element is connected to the receiving part, the method further comprises attaching the insert piece to the first head prior to connecting the first anchoring element to the receiving part.

27. A polyaxial bone anchoring system comprising:
- a receiving part having a first end and a second end, a central axis extending through the first end and the second end, a transverse channel at the first end for receiving a rod, and an accommodation space having an opening at the second end;
- a first anchoring element having a first shank for anchoring in a bone or a vertebra and a first head a sleeve-like insert piece configured to be arranged around a portion of the first head and to be arranged in and pivot in the accommodation space of the receiving part, such that an angle formed by a central axis of the insert piece with the central axis of the receiving part is adjustable when the insert piece is in the accommodation space;
- a second anchoring element having a second shank for anchoring in a bone or a vertebra and a second head having a first portion having a width corresponding to a width of the insert piece and a second portion having a width corresponding to a width of the first head, wherein the first head with the insert piece and the second head are each configured to be introduced into the accommodation space through the opening, such that the first bone anchoring element and the second bone anchoring element are configured to be interchangeably connectable to the receiving part; and
- a pressure member configured to be arranged at least partially in the accommodation space, the pressure member comprising a portion configured to contact the first head or the second head to exert pressure onto the first head or the second head when the pressure member and one of the first head or the second head are arranged in the receiving part;
- wherein when one of the first anchoring element or the second anchoring element is connected to the receiving part, the connected anchoring element is pivotable relative to the receiving part and can be locked at an angle relative to the receiving part by exerting pressure with the pressure member onto the respective head of the connected anchoring element.

* * * * *